United States Patent [19]
Parker et al.

[11] Patent Number: 4,687,785
[45] Date of Patent: Aug. 18, 1987

[54] THERMALLY ADAPTIVE POLYMERS AND PREPOLYMERS AND METHODS OF MAKING IN WHICH AN IMIDE IS FORMED FROM A POLYANHYDRIDE OLIGOMER AND AN ISOCYANATE

[75] Inventors: John A. Parker, Los Altos, Calif.; Rubin Feldman, Ladue; Robert L. Bryant, Webster Groves, both of Mo.

[73] Assignee: Thermal Science, Inc., St. Louis, Mo.

[21] Appl. No.: 769,863

[22] Filed: Aug. 27, 1985

[51] Int. Cl.$^4$ .............................................. C08G 18/14
[52] U.S. Cl. .................................. 521/106; 521/157; 528/51; 528/73
[58] Field of Search .................. 521/106, 157; 528/51, 528/73

[56] References Cited

U.S. PATENT DOCUMENTS

| | | | |
|---|---|---|---|
| 3,620,987 | 11/1971 | McLaughlin et al. | 260/2.5 N |
| 3,716,519 | 2/1973 | Yoda et al. | 528/73 |
| 3,954,710 | 5/1976 | Bower et al. | 528/51 |
| 3,966,652 | 6/1976 | Gagliani et al. | 260/2.5 N |
| 4,184,021 | 1/1980 | Sawko et al. | 521/106 |
| 4,241,193 | 12/1980 | Gagliani | 521/77 |
| 4,305,796 | 12/1981 | Gagliani et al. | 521/185 |
| 4,316,843 | 2/1982 | Waitkus et al. | 528/185 |
| 4,338,427 | 7/1982 | Maekawa et al. | 528/51 |
| 4,360,604 | 11/1982 | Gagliani et al. | 521/189 |
| 4,439,381 | 3/1984 | Gagliani et al. | 264/26 |

Primary Examiner—Maurice J. Welsh
Attorney, Agent, or Firm—Polster, Polster & Lucchesi

[57] ABSTRACT

Reaction of an aromatic dianhydride with a polycyclic aromatic primary diamine at a controlled reaction rate yields a diamic acid dianhydride oligomer. The oligomer may be a precursor for an imide foam which forms at low temperature, has outstanding physical characteristics, and is extremely heat resistant. The diamic acid moiety may be converted to diimide, and other modifications of the oligomer are disclosed. Other derivatives of the oligomers are also disclosed.

59 Claims, No Drawings

THERMALLY ADAPTIVE POLYMERS AND PREPOLYMERS AND METHODS OF MAKING IN WHICH AN IMIDE IS FORMED FROM A POLYANHYDRIDE OLIGOMER AND AN ISOCYANATE

BACKGROUND OF THE INVENTION

This invention relates to novel diamic precursors for polymers, to novel polymers, and to novel reactions involving the precursors.

The invention is particularly concerned with the production of a novel oligomer which is useful in the production of imide foams. It is also concerned with novel imide foams and other products formed from the oligomer. It is also concerned with the processing of imide foams and their precursors, to provide greatly improved handling and mechanical properties of the materials.

Polyimide (imide) foams have been known for over thirty years. An early example of such foams is the reaction product of pyromellitic dianhydride (PMDA) with a polymethylene polyphenylisocyanate (PAPI). These foams have great heat resistance but they have not found general acceptance because they require a high cure temperature to produce the foam, they are physically weak and friable, they shrink when heated, and they are incompatible with fillers which are used in other foam systems to give the foam desirable qualities.

Many attempts have been made to improve the qualities and the ease of manufacture of imide foams.

For example, U.S. Pat. No. 3,620,987 eliminates the need for external heat by reacting a polycarboxylic acid or a polycarboxylic anhydride with a polyisocyanate in the presence of a catalyst comprising a tertiary amine and an aliphatic alcohol containing one to six carbons. In U.S. Pat. No. 4,184,021, to Sawko, Riccitiello, and Hamermesh, the imide foam is formed by reacting PMDA with PAPI in the presence of a surfactant, a strong acid, and furfuryl alcohol to generate heat internally. These approaches require extreme care and produce a foam which is friable and lacks strength.

Several patents to Gagliani and associates (e.g., U.S. Pat. Nos. 4,439,381, 4,360,604, 4,305,796, 4,241,193, and 3,966,652) disclose imide foams which have superior physical properties, such as strength, flexibility, and ability to be filled. The physical properties are nonetheless not ideal, and such properties as flexibility are obtained only by using flammable additives. The foams also shrink when they are exposed to flame or thermal extremes, and therefore are not well adapted to protecting substrates from fire conditions. These foams, moreover, must be formed and cured at greatly elevated temperatures. Their use is therefore limited to relatively small products, and producing these products requires expensive and cumbersome equipment.

Presently known imide foams are also limited to relatively low density material unsuitable for structural use.

The cost of PMDA has also limited the wide application of imide foams.

In numerous other situations, fire- and heat-resistant polymers are required. For example, high temperature fibers, high temperature coatings, and binders for high temperature composites are widely sought.

SUMMARY OF THE INVENTION

One of the objects of this invention is to provide a heat resistant imide foam which can be produced in situ at low temperature.

Another object is to provide such a foam which has outstanding physical properties, such as strength, flexibility and uniform cell size.

Another object is to provide such a foam which is relatively inexpensive to manufacture and which is formed from easily handled materials.

Another object is to provide such a foam which will readily accept fillers up to a large percentage of the weight of the foam.

Another object is to provide such a foam which may selectively be made closed porosity or open porosity, and which may selectively be made with a wide range of density, for example from one pound per cubic foot to over ten pounds per cubic foot.

Another object is to provide such a foam which is extremely resistant to fire conditions, which provides a high char yield under these conditions, which does not shrink appreciably under these conditions, which maintains its strength under these conditions, and which does not produce substantial quantities of flammable or noxious gases under these conditions.

Another object is to provide a novel precursor for forming such foams.

Another object is to provide such a precursor which is capable of forming novel coatings, and other useful compounds, as well as the novel foams of the invention.

Another object is to provide a novel reaction between an aromatic dianhydride reactant and a polycyclic aromatic primary diamine reactant to form novel trimeric dianhydride precursors for polymers.

Another object is to provide a family of novel diamic acid oligomers.

Another object is to provide a family of novel dianhydrides and methods for making them.

In accordance with one aspect of this invention, generally stated, a novel oligomer is provided which includes reactive terminal groups and two amic acid groups, each amic acid group consisting of a carboxyl group and a singly substituted amide linkage attached to adjacent carbon atoms. Preferably, the adjacent carbon atoms are members of an aromatic ring. The oligomer preferably has a molecular weight of from about 400 to about 1000, most preferbly from about 600 to about 1000.

Preferably, most of the atoms of the oligomer are either parts of a ring structure or are attached directly to a ring structure or are part of the amic acid group. Preferably, over ninety percent of the molecular weight of the oligomer consists of atoms so attached. This arrangement provides few unprotected portions of the polymers produced from the oligomers, and the polymers formed from the oligomers are therefore extremely resistant to degradation by fire and high temperature.

In the preferred embodiment, the terminal groups of the oligomer are anhydride groups. In another embodiment, the terminal groups are amines. Although not presently preferred, the terminal anhydride groups may be hydrolyzed to carboxyl groups, thereby forming a tetracarboxylic acid diamic acid.

The amic acid groups may be converted to imide linkages by dehydration, as by reaction with acetic anhydride, to provide a diimide oligomer. This oligomer is a starting material for a variety of polymeric materials.

In accordance with another aspect of the invention, a method of producing an amic acid oligomer is provided, comprising reacting an aromatic or alicyclic dianhydride reactant with an aromatic primary diamine reactant, and controlling the reaction conditions to provide a substantially pure trimer consisting of two terminal parts derived from one of the reactants and a central part derived from the other reactant. Preferably, at least one of the reactants is carried by a solvent in which it is poorly soluble.

In the preferred embodiment, the dianhydride is pyromellitic dianhydride (PMDA). Other aromatic dianhydrides may also be used, such as benzophenone dianhydride, or a polycyclic aromatic dianhydride. Examples of suitable aromatic dianhydrides are given, for example, in U.S. Pat. No. 4,316,843, to Waitkus and D'Alelio.

Alicyclic tetracarboxylic acid polyanhydrides may also be usable in forming the oligomers of the invention. For example, a novel family of polyalicyclic polyanhydrides may be used. These anhydrides are formed by polymerizing cis-5-norbornene-2,3-dicarboxylic acid anhydride with a catalyst. A preferred catalyst is a Lewis acid, most preferably boron trifluoride etherate. The resulting materials have more than one anhydride per molecule, and the average number of anhydrides per molecule, and the distribution of anhydrides per molecule, may be controlled by controlling reaction conditions and proportions of reactants and catalyst.

The diamine is preferably sterically hindered to help control the reaction rate. In the preferred embodiment, the diamine is 3,3' dichloro 4,4' diamino diphenylmethane (MOCA). Other suitable aromatic diamines, particularly ortho-substituted aromatic diamines, are set out, for example, in Waitkus and D'Alelio, U.S. Pat. No. 4,316,843. MOCA has characteristics which make it well suited for forming quantitatively a desirable oligomer: steric hindrance, for reducing the rection rate and suppressing chain formation in the production of the oligomer; solubility in common solvents such as EHF, DMF, and ketone solvents; and asymmetry, to give the oligomer a certain degree of plasticity, for example a softening point of from 20° to 80° C. When the oligomer is reacted to form a polymer, this diamine releases a limited quantity of chlorine, to act as a transpirational coolant, a radical scavenger, and (by its removal from the polymer under thermal extremes) as a means of permitting additional thermal cross-linking under fire conditions, thereby providing the polymer with great dimensional stability under a fire or heat load.

The reaction rate of the oligomer-forming reaction is further controlled by the use of a solvent in which the reactants are only slighly soluble. In the preferred embodiment, the dianhydride is partially dissolved and partially suspended in a solvent consisting of tetrahydrofuran and a smaller amount of dimethylacetamide, and the diamine is added slowly to assure that the reaction proceeds as a termination reaction, rather than as a chain-propagating reaction. The reaction rate is also controlled by maintaining the temperature of the reaction below about 70° C.

The oligomer is extracted from the reaction mixture by solvent partition or by absorption after vacuum evaporation of excess solvent.

In one preferred embodiment, addition of a water-insoluble ammonium polyphosphate to the oligomer absorbs solvent and converts the oligomer from a sticky liquid to a flowable powder. In another embodiment, the pure oligomer is precipitated by partition of the solvent with cyclohexane.

In another embodiment of the method of making an oligomer, the diamine form of the oligomer is formed by suspending a dianhydride, such as PMDA, in a poor solvent, such as methyl isobutyl ketone, and adding a solution of diamine in a good solvent, such as methyl ethyl ketone. The diamine trimer is formed instantly and precipitates at room temperature.

In accordance with another aspect of the invention, the dianhydride oligomers are reacted with an aromatic diisocyanate, such as polymethylene polyphenylisocyanate (e.g., PAPI 901), in the presence of a small amount of water and a tertiary amine catalyst at room temperature to form chemically stable, heat resistant, dimensionally stable imide forms. Preferably, the reaction mixture also includes a lower molecular weight dianhydride such as PMDA, to provide greater reaction heat. The novel mixed norbornene polyanhydrides of the invention may also be used for the lower molecular weight dianhydride.

Preferably, the foam is postcured at an elevated temperature of around 150° C. to close the amic acid moieties to imide rings. Curing at 150° C. causes the foam to turn a brighter yellow-orange, and appears to cause the amic acid moieties of the oligomers to close into imide rings. Curing at even higher temperatures, in the range of 200° C., causes the foam to turn brick red, with the apparent loss of chlorine atoms from the oligomer and formation of a cardopolymer. Curing at room temperature is believed to cause excess isocyanate in the foam formulation to react with atmospheric moisture to form urea terminations which are less fire resistant than the carbodiimide terminations formed at higher temperatures.

Both the room temperature cured foams and those cured at elevated temperatures show physical characteristics equivalent to a good polyurethane, and maintain those characteristics at elevated temperatures. The foams cured at elevated temperature show somewhat better physical characteristics at room temperature and show better resistance to heat and fire, although foams cured both ways are outstanding both at room temperature and under extreme fire and heat conditions. The foams are high temperature foams, that is, they are suitable for continuous service without significant changes in mechanical or physical properties over a temperature range of from 350° to 500° F. and show substantially no shrinkage under a heat load of from three to twenty watts per square centimeter. They are also fire resistant, that is, they show excellent flammability resistance, flame spread values below 5, limiting oxygen index values above 80, virtual freedom from smoke and toxic gas emissions at applied heat loads above ten watts per square centimeter, and effective heats of ablation of greater than 3000 BTU's per hour.

The foam is self-generating, by release of carbon dioxide in the imidazation reaction with isocyanate, and the entire process may be carried out using conventional foam-in-place polyurethane spray equipment.

Because the foaming reaction is uncoupled from the polymerization reaction, the density of the imide foam is controllable to permit relatively high density foams as well as low density foams. By varying the amount of water, the density of the foam may be varied from as low as about one pound per cubic foot to over three pounds per cubic foot at atmospheric pressure. By increasing the pressure, as by enclosing the foaming reaction in a mold, the density of the foam may be increased to over ten pounds per cubic foot.

The prereaction of the amine with the dianhydride suppresses side reactions of the isocyanate with amine which would form thermally unstable urea groups. Moreover, the molecular weight of the oligomer is sufficiently high that the foam has acceptable mechanical properties and the foaming polymerization (formation of imide linkages and release of carbon dioxide as blowing agent) takes place at room temperature, even though many of the preformed amic acid groups do not react to close their imide rings.

The imide foam formed from the amic acid oligomers at room temperature contains a "hidden" amic acid functionality which reacts at moderately elevated temperatures to produce an imide ring. The closing of the imide ring does not change the cell structure, the major physical properties, or the geometry of the foam, and the foam merely converts to an increasingly highly temperature resistant foam as its temperature is increased above a critical temperature, about 120° C. in the preferred embodiment. At higher temperatures the chlorine of the preferred foam is released as a free radical, and the aromatic ring to which it is attached cross links with other aromatic rings to form a cardopolymer. The chlorine of the preferred embodiment thus acts as a second hidden functionality. The formation of the cardopolymer also does not appreciably change the cell structure or the geometry of the foam. It will thus be seen that the foam may be cured at temperatures ranging from room temperature to over 200° C., without substantially changing the geometry of the foam. It will also be seen that the foam, however cured, will maintain its geometry under conditions of high temperature and fire.

The addition of inorganic fillers to the imide foam-producing reaction mixture greatly increases the strength and ablative qualities of the imide foam chars. The imide foams of the present invention are uniquely capable of being heavily filled, up to 50% by weight or more, with inorganic fillers such as glass fibers or glass microballoons, without compromising their foamability, structure, and ease of processing.

The amic acid oligomers may be converted to imides, by dehydration of the amic acid moieties. The imide oligomers derived from the amic acid oligomers have much higher melting points, and are therefore more difficult to process into foams. They may be processed into foams by preheating the reactants, for example to about 65° C. in the preferred embodiments.

Both the amic acid oligomers and their derivative imide oligomers are also useful for producing high temperature polymeric coatings. For example, the preferred amic acid oligomer, when reacted with isocyanate (PAPI 901) in the absence of water produces a clear hard coating which foams on application of intense heat.

The diamine-terminated oligomer may be reacted with difunctional oligomers or monomers, such as dianhydrides, diepoxides, or dialdehydes such as terephthalaldehyde, to produce high-temperature, fire-resistive polymers.

The tetracarboxylic acid diamic acid oligomer may be foamed with polyisocyanate at room temperature. The foam has excellent physical properties, but because amide linkages predominate over imide linkages, it does not have the same high temperature resistance as does the foam formed from the dianhydride.

Other aspects of the invention will be better understood by those skilled in the art in the light of the following description of the preferred embodiments.

DESCRIPTION OF THE PREFERRED EMBODIMENT

The following examples are illustrative of the oligomers, polymeric foams, and methods of the present invention.

EXAMPLE 1

Synthesis of Diamic Acid Dianhydride Oligomer (DADA)

The diamic acid dianhydride oligomer of pyromellitic dianhydride (PMDA) and 3,3' dichloro 4,4' diamino diphenyl methane (MOCA) is prepared by dissolving 436.24 gms. (2 moles) of PMDA in 164.90 gms. of a solvent mixture consisting of 1234.0 gms. tetrahydrofuran and 411.50 gms. of dimethylacetamide. Some of the pyromellitic dianhydride remains in suspension. A second solution is prepared by dissolving 269.16 gms. of MOCA in a solvent mix of 201.87 gms. of tetrahydrofuran and 67.29 gms. of dimethyacetamide.

The 538.2 gms. of the second solution containing MOCA is slowly added to the solution of PMDA over a 60 minute period. Stirring and heating are applied at such a rate that the reaction mixture increases in temperature from 25° C. to 70° C.

The solvated diamic acid dianhydride oligomer is then stripped of solvent at 40° C.–70° C. with a 20-25 in Hg vacuum over 4 hours. The oligomer obtained is a sticky glass melting at 60° C. The oligomer is hereinafter referring to as DADA (diamic acid dianhydride) and has the formula:

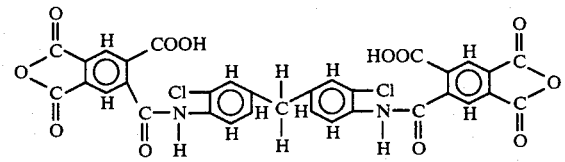

EXAMPLE 2

Procedure for Synthesis of the Diacid Dianhydride Oligomer from Benzophenone Dianhydride and 3,3' Dichloro-4,4' Diamino Diphenylmethane The diamic acid dianhydride oligomer of benzophenone dianhydride and 3,3' dichloro—4,4' diamino diphenyl methane (MOCA) is prepared by dissolving 644.40 gms. (2 moles) of benzophenone dianhydride in 1645.90 gms. of a solvent containing 1234.0 gms. of tetrahydrofuran and 411.50 gms. of dimethylacetamide. Some benzophenone dianhydride remains in suspension. A separate solution of MOCA is prepared by dissolving 269.16 gms. (1 mole) of MOCA into 269.12 gms. of solvent comprising 201.87 gms. of tetrahydrofuran, and 67.29 gms. of dimethylacetamide.

The solution of MOCA is added over a period of 1 hour to the solution of benzophenone dianhydride, with stirring at such a rate that the reaction mixture increases in temperature from 25° to 70° C.

The diamic acid dianhydride oligomer (DADA-2) is obtained by solvent removal through heating to 70° C.

maximum temperature and applying a vacuum to 23" of mercury for 4 hours. The result is a sticky glass of amber color melting at 60° C.

EXAMPLE 3

Imidization of Diamic Dianhydride (DADI)

The dianhydride diimide (hereinafter DADI) of DADA, formed in accordance with EXAMPLE 1, is prepared by dissolving 416.0 gms. of DADA, in 416.0 gms. of dimethylformamide. 61.26 gms. (0.60 moles) of acetic anhydride is added to the reaction mixture and refluxed for one hour at 120° C. After removal of solvent at 100°-120° C. the DADI is obtained as a white solid melting at 210° C. and is used in foam formulations without further purification.

EXAMPLE 4

Synthesis of Norbornene Maleic Anhydride and Mixed Anhydrides

Mixed polybasic anhydride containing a plurality of 1,2 anhydrides is obtained by distilling, at 200° C., 66.10 gms. (1 mole) of cyclopentadiene directly from dicyclopentadiene into a reactor containing 98.06 gms. (1 mole) of maleic anhydride, heated to a temperature of 55° C. When the transfer is complete, the reaction mixture is heated to 100° C. for 2 hours. The reaction mixture is then stripped of any excess cyclopentadiene at 120° C. at 1 atmosphere. The resulting Diels-Adler adduct of cyclopentadiene and maleic anhydride is the anhydride of cis-5-norbornene-2,3-dicarboxylic acid. The reaction mixture is cooled to 50° C., and 4.90 gms. (0.03 moles) of boron trifluoride etherate is added slowly with stirring. The reaction mixture exotherms to 65° C. after which it is heated to 125° C., to decompose the $BF_3OEt$ and then cooled. The reaction is quenched by mixing with 3 liters of 10% sodium bicarbonate. The mixture is then neutralized with dilute 5% hydrochloric acid. The mixed polybasic anhydride of norbornene-2,3-dicarboxylic acid anhydride is obtained as a fine tan power, Mp. 200° C., and used for foam preparation without further purification.

EXAMPLE 5

Process for Preparation of Solvated Diamic Dianhydride for Use in Foam Formulations A first foam ingredient is obtained as a finely divided free flowing powder by first chilling the DADA oligomer obtained in EXAMPLE 1 to 0° C., and pulverizing it. To the DADA is added an equal weight of water-insoluble ammonium polyphosphate (solubility of 1.5% or less). A suitable ammonium polyphosphate is sold by Monsanto as Phoscheck P-30. The mixture is further pulverized to give the solvated DADA foam ingredient. This ingredient is used in foam formulation as obtained.

EXAMPLE 6

Preparation of Solid Foam Ingredient B

The DADA obtained as a sticky glass in EXAMPLE 1, is crystalized to a finely divided free flowing powder with softening point between 60°-70° C. as follows. The DADA, after solvent stripping as described in EXAMPLE 1, is worked with 2000 mls of cyclohexane, separated and dried in vacuo. The solid residue is ground to a fine tan powder between 200-400 mesh, melting at 60°-70° C. and used in foam formulations without further purification. The crystallized pure diamic acid oligomer has a molecular weight of 703.25, consistant with the formation of a pure dianhydride terminated trimer.

EXAMPLE 7

Foam A

Low density (1-3 lbs/cu ft) resilient, mainly closed cell, high temperature, and extremely fire resistant imide foams are prepared from the solvated foam ingredient of EXAMPLE 5 (a 1:1 blend of "glassy", resinous DADA and ammonium polyphosphate) by means of a free blow of a two part ambient temperature foaming system comprised as follows:

| Component | Parts (by weight) |
|---|---|
| PART A | |
| 1. Pyromellitic Dianhydride | 3.0 |
| 2. Polyaniline Isocyanate (PAPI) | 8.0 |
| 3. DADA/Ammonium Polyphosphate (1:1) | 3.0 |
| PART B | |
| 4. Water | 0.3 |
| 5. DC-193 (surfactant - Dow Corning) | 2.0 |
| 6. NiAX A-1 (amine accelerator - Union Carbide) | 0.35 |
| 7. Diethanolamine | 0.40 |

The foam A is prepared by rapidly mixing Part A and Part B together at room temperature, and pouring into an open mold. Foaming occurs at once, producing an exotherm which reaches a maximum of 80° C. in one minute. Tack-free closed cell foam which can be removed from the mold at room temperature is obtained in approximately one hour. Post curing for several days at room temperature completes the first stage of the cure.

The foam will react further at 150° C., closing all of the amic acid rings to give a bright-yellow foam with no change in overall dimensions, free of friability and with optimum mechanical properties. This foam may be heated to 500°-600° C. without change in shape, and with very low shrinkage, to give a char yield of between 80-90 percent. Foams prepared in this manner post cured at temperatures in excess of 150° C. are virtually incombustible giving no flame spread or smoke, without significant change in mechanical properties. The room temperature mechanical and physical properties obtained for foam are similar to a typical resilient polyurethane foam in a density range of 2-3 lbs/cu ft.

The available combination of properties, mechanical strength, high temperature resistance, fire resistance and flammability of DADA-derived foams is largely a matter of the choice of pure conditions as outlined in the following table.

| Cure Temperature | Room Temperature | 150° C. | 200° C. |
|---|---|---|---|
| Mechanical Strength | Fair | Excellent | Good |
| High Temperature | Fair | Excellent | Excellent |
| Fire Resistance | Good | Excellent | Excellent |
| Flammability | Fair | Good | Non-Combustible |

These combinations of properties are not available with other imide foams.

EXAMPLE 8

Composite Derivatives of Foam A (Foam A-1)

Amic acid foams as described in EXAMPLE 7, unlike other imide foams, are extremely tolerant to loading with high concentrations of inorganic fibers and fillers.

A blend of 0.9 parts of chopped fiberglass and 0.9 parts of glass microballoons were mixed with 14.0 parts of Part A, as described in EXAMPLE 7. After thorough wetting of fillers, the premixed Part A was mixed with 2.5 parts of Part B to give a room temperature pour in low mix. An open mold, six inches deep, was filled with this composition. Foaming occurs at once with a much lower rise time than Foam A alone. The sample cured tack free in 1 hour and could be mechanically handled. After 1 hour, it was removed from the mold and cured at 150° C. to give a uniformly reinforced composite foam with a density of 3.0–3.5 lbs/cu ft.

This foam was aged for 24 hours at 200° C. with no loss in dimensional stability and no apparent change in mechanical properties.

Under the impact of a propane torch, the foam converted to an identical shape of tough carbonaceous debris layer which was extremely tough and erosion resistant. This foam exhibited qualitatively no apparent flame spread or after-burning.

A four inch section of this 3.0 lbs/cu ft foam was evaluated for 3 hours in a standard E119 test and gave a back face temperature rise of 250°–300° F. with no shrinkage and excellent fire containment.

EXAMPLE 9

Composite Structual Foam (Foam A-2)

A 30 gm sample of the premix described in EXAMPLE 8 was poured into a 4"×2"×1" steel mold and closed. It was allowed to compress under the ambient pressure generated by the blowing process at 25° C. When the foaming process was complete, the sample was cured at 200° C. for 2 hours. After removal from the mold a tough, extremely strong 12–13 lb/cu ft density closed porosity foam was obtained which exhibited thermal properties similar to the foam sample prepared in accordance with EXAMPLE 8.

EXAMPLE 10

Low Density Foam From Preformed Dianhydride Diimide (Foam B)

Acceptable high performance foams were prepared from formulations in which DADA was replaced with DADI as described in EXAMPLE 3. Because of the higher melting point of DADI, these foams cannot be prepared easily at room temperature.

A two part foam system was prepared as follows:

| Components | Parts (by weight) |
|---|---|
| Part A | |
| 1. PMDA | 3.0 |
| 2. PAPI 901 | 8.0 |
| 3. DADI | 3.0 |
| Part B | |
| 4. H$_2$O | 0.3 |
| 5. DC193 | 1.0 |
| 6. Diethanolamine | 0.4 |
| 7. NiAX A-1 | 0.35 |

Both Part A and B were preheated to 65° C. before mixing. The rise time and cure time were considerably longer than with DADA.

The resulting imide foam from DADI exhibits only fair cell structure, and a density of 5–6 lbs/cu ft. The samples required curing at 150° C. to achieve acceptable mechanical properties in the standard formulation. All foams prepared by this procedure gave similar high temperature and fire resistance but remarkably improved flammability resistance at a cure temperature of 150° C.

EXAMPLE 11

Foam Production Through General Purpose Two Part Urethane Foam Machine

To evaluate the processability of the imide foam system in standard urethane foam machines, at room temperature without heating, a convenient two part machine formulation was formulated as follows:

| Component | Parts (by weight) |
|---|---|
| Part A | |
| 1. Pyromellitic Dianhydride | 7.93 |
| 2. PAPI 901 | 21.16 |
| 3. DADA (EXAMPLE 6) | 3.97 |
| Part B | |
| 4. DC-193 | 5.38 |
| 5. H$_2$O | 0.95 |
| 6. Diethanolamine | 0.41 |
| 7. NiAX A-1 | 0.14 |

Part A and B were introduced into separate pressure pots. An air impinging mixing head was fed a metered ratio of 4:1 (Part A:Part B) at a throughput of 2 lbs/min. The run was fed into rectangular molds 4"×4"×3" and filled so that the expanded foam just filled up the mold. The cream time and viscosity change with time were such that complete filling of the mold gave a foam of between 3–4 lbs/cu ft. The molds were immediately transfered to a 150° C. oven and samples postcured to 150° C. for 1 hour, after which the foam board stock could be easily removed from the mold. A bright-yellow foam of excellent texture and cell size was obtained with excellent mechanical properties. It gave the same high temperature and fire properties as shown in EXAMPLE 7.

Blocks of this foam were post cured for 5–10 hours at 200° C. without significant change in mechanical properties and dimensionality to give a completely non-combustible foam.

EXAMPLE 13

Foam C High Resiliency, High Temperature Foams From Mixed Anhydrides of Norbornene Anhydride The Pyromellitic Dianhydride used in the foregoing example can be replaced on a one to one basis with the norbornene polyanhydride of EXAMPLE 4 to give an excellent high temperature and fire resistant foam of exceptional resiliency, small cell size and good texture.

A two part system is prepared as follows:

| Component | Parts |
|---|---|
| Part A | |
| 1. Norbornene polyanhydride | 3.0 |
| 2. DADA | 3.0 |
| 3. PAPI | 8.0 |

-continued

| Component | Parts |
|---|---|
| Part B | |
| 4. H$_2$O | 0.3 |
| 5. DC-193 | 1.0 |
| 6. Diethanolamine | 0.4 |
| 7. NiAX A-1 | 0.35 |

The foam is obtained by mixing Part A and Part B vigorously at room temperature. Foaming takes place at once to give a 3.0 lb/cu ft foam of cream color with extremely fine and uniform cell size. The foam is cured at 200° C. to give a foam comparable in thermal properties with the previous examples but with much improved resiliency.

We claim:

1. A polymeric foam consisting of repetitive units, each of said units comprising an imide linkage and an amic acid group, said amic acid group consisting of a carboxyl group and a singly substituted amide linkage attached to adjacent carbon atoms.

2. The polymeric foam of claim 1 wherein, upon heating the polymer, the carboxyl group and the amide linkage condense to form an imide linkage, thereby stabilizing the polymer against heat degradation.

3. The polymeric foam of claim 2 wherein each repetitive unit of the polymer includes two said amic acid linkages and wherein said adjacent carbon atoms of each of said amic acid groups are members of aromatic rings.

4. The polymeric foam of claim 3 wherein said amide linkage includes a carbon atom attached to an aromatic ring at a position ortho to said carboxyl group and a nitrogen atom attached to another aromatic ring, said other aromatic ring being substituted at a position ortho to said nitrogen.

5. The polymeric foam of claim 3 wherein said imide linkage is to an aromatic ring, wherein a halogen atom is attached to at least one of said rings, and wherein, upon heating the polymer to a temperature in excess of the temperature at which the carboxyl group and the amide linkage condense, said halogen atom is released from said at least one ring, said ring cross-linking with at least one other said ring to form a cardopolymer.

6. The polymeric foam of claim 5 wherein each said repetitive unit has a molecular weight of from about 600 to about 1000, and wherein said polymeric foam has a density of from about one to about thirteen pounds per cubic foot.

7. In the method of forming an imide foam at room temperature without applying external heat, said method comprising mixing an isocyanate and a polyanhydride oligomer in the presence of a catalyst, the improvement wherein said polyanhydride oligomer includes two amic acid groups, each of said amic acid groups consisting of a carboxyl group and a singly substituted amide linkage attached to adjacent carbon atoms.

8. The improvement of claim 7 wherein said polyanhydride oligomer has a molecular weight of from 600 to 1000 and has a softening point of from 20 degrees Celsius to 80 degrees Celsius.

9. The improvement of claim 8 wherein said polyanhydride oligomer is mixed with a water-insoluble ammonium polyphosphate.

10. The improvement of claim 8 wherein said oligomer has the structure:

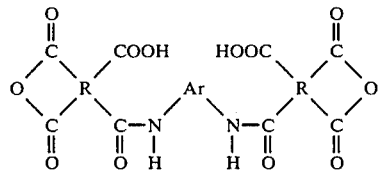

where R is a substituted or unsubstituted alicyclic, polyalicyclic, aromatic or polyaromatic group and Ar is a substituted or unsubstituted aromatic or polyaromatic group.

11. The improvement of claim 10 wherein Ar includes two aromatic rings, each nitrogen linkage shown in claim 10 being to a different one of said aromatic rings, each of said two aromatic rings being substituted in a position ortho to the nitrogen linkage.

12. The improvement of claim 11 wherein each of said two aromatic rings is substituted, in a position ortho to the nitrogen linkage, by a halogen.

13. The improvement of claim 7 wherein said polyanhydride oligomer and said isocyanate are mixed in the presence of water.

14. The improvement of claim 13 wherein said polyanhydride oligomer is mixed with a water-insoluble ammonium polyphosphate.

15. The improvement of claim 7 further including a step of curing said imide foam at a temperature of at least about 150 degrees Celsius.

16. The improvement of claim 7 wherein said method further comprises mixing another polyanhydride with said first mentioned polyanhydride, said second polyanhydride being chosen from the group consisting of pyromellitic dianhydride, benzophenone dianhydride, and a norbornene polycarboxylic acid anhydride.

17. In the method of foaming an imide polymer by mixing an isocyanate and a polyanhydride oligomer in the presence of a catalyst, the improvement wherein said polyanhydride oligomer is chosen from the group consisting of diamic acid dianhydrides and diimide dianhydrides.

18. The improvement of claim 17 wherein said polyanhydride oligomer is mixed with a water-insoluble ammonium polyphosphate.

19. The improvement of claim 17 wherein said polyanhydride oligomer is a dianhydride having the structure:

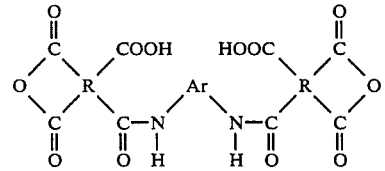

where R is a substituted or unsubstituted alicyclic, polyalicyclic, aromatic or polyaromatic group and Ar is a substituted or unsubstituted aromatic or polyaromatic group.

20. The improvement of claim 19 wherein Ar includes two aromatic rings, each nitrogen linkage shown in claim 19 being to a different one of said aromatic rings, each of said two aromatic rings being substituted, in a position ortho to the nitrogen linkage, by a halogen.

21. The improvement of claim 20 including a further step of heating said polymer to a temperature of at least about 200 degrees Celsius to remove said halogens and convert said polymer to a cardopolymer.

22. The improvement of claim 17 wherein said oligomer has the structure:

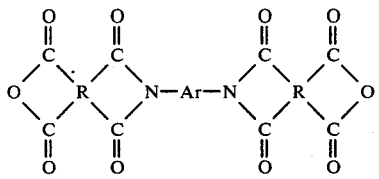

where R is a substituted or unsubstituted alicyclic, polyalicyclic, aromatic or polyaromatic group and Ar is a substituted or unsubstituted aromatic or polyaromatic group.

23. The improvement of claim 22 wherein ar includes two aromatic rings, each nitrogen linkage shown in claim 22 being to a different one of said aromatic rings, each of said two aromatic rings being substituted, in a position ortho to the nitrogen linkage, by a halogen.

24. The improvement of claim 23 including a further step of heating said polymer to a temperature of at least about 200 degrees Celsius to remove said halogens and convert said polymer to a cardopolymer.

25. The improvement of claim 17 wherein said polyanhydride is at least in part a diamic acid, and wherein said method includes a step of heating said polymer to a temperature of at least about 150 degrees Celsius to dehydrate said diamic acid to an imide ring.

26. The improvement of claim 17 wherein said imide polymer is a foam.

27. The improvent of claim 26 wherein said imide foam is filled with an inorganic filler.

28. In the method of forming an imide polymer by mixing an isocyanate and polyanhydride oligomer in the presence of a catalyst, the improvement wherein said polyanhydride oligomer includes two internal groups preformed in said oligomer, said internal groups being chosen from the group consisting of imide and amic acid, said internal groups each including a nitrogen atom attached to an aromatic ring, said aromatic ring being substituted by a halogen in a position ortho to the nitrogen linkage.

29. The improvement of claim 28 including a further step of heating said polymer to a temperatue of at least about 200 degrees Celsius to remove said halogens and convert said polymer to a cardopolymer.

30. In the method of forming an imide polymer by mixing an isocyanate and polyanhydride oligomer in the presence of a catalyst, the improvement wherein said polyanhydride oligomer includes two amic acid groups preformed in said oligomer, said amic acid groups each including a nitrogen atom attached to an aromatic ring, said aromatic ring being substituted in a position ortho to the nitrogen linkage.

31. The improvement of claim 30 including a further step of heating said polymer to a temperature of at least about 150 degrees Celsius to close said amic acid groups into imide linkages, and including another further step of heating said polymer to a temperature of at least about 200 degrees Celsius to convert said polymer to a cardopolymer.

32. A high temperature resistant polymer consisting of repetitive units, each of said units comprising an imide linkage and two amic acid groups, each said amic acid group consisting of a carboxyl group and a singly substituted amide linkage, the amide linkage including a carbon atom attached to a first ring in a position ortho to the carboxyl group and a nitrogen atom attached to a second ring, the second ring being substituted ortho to the nitrogen atom.

33. The polymer of claim 32 wherein the second ring is substituted ortho to the nitrogen atom by a halogen atom, said halogen atom being removable by the application of heat to cross-link at least some of said units to form a cardopolymer.

34. In the method of forming an imide polymer by mixing an isocyanate and a polyanhydride oligomer in the presence of a catalyst, the improvement wherein said polyanhyride oligomer is chosen from the group consisting of diamic acid polyanhydrides and diimide polyanhydrides, and wherein said oligomer is mixed with a substantially water-insoluble ammonium polyphosphate.

35. The improvement of claim 34 wherein said method further comprises mixing another polyanhydride with said polyanhydride oligomer, said second polyanhydride being chosen from the group consisting of pyromellitic dianhydride, benzophenone dianhydride, and a norbornene polycarboxyic acid anhydride.

36. In the method of forming an imide polymer by mixing an isocyanate and a polyanhyride oligomer in the presence of a catalyst, the improvement wherein said polyanhydride oligomer is chosen from the group consisting of solid diamic acid polyanhydrides and solid diimide polyanhydrides.

37. The improvement of claim 36 wherein said polyanhydride oligomer has a molecular weight of from 400 to 1000 and has a softening point of from 20 degrees Celsius to 80 degrees Celsius.

38. The improvement of claim 36 wherein said polyanhydride oligomer is mixed with a water-insoluble ammonium polyphosphate.

39. The improvement of claim 36 wherein said oligomer has the structure:

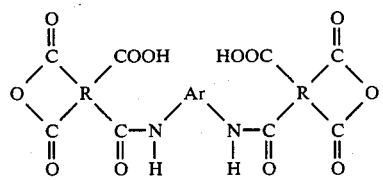

where R is a substituted or unsubstituted alicyclic, polyalicyclic, aromatic or polyaromatic group and Ar includes two aromatic rings, each nitrogen linkage shown above being to a different one of said aromatic rings, each of said two aromatic rings being substituted in a position ortho to the nitrogen linkage.

40. The improvement of claim 39 wherein each of said two aromatic rings is substituted, in a position ortho to the nitrogen linkage, by a halogen.

41. The improvement of claim 39 further including a step of curing said imide foam at a temperature of at least about 150 degrees Celsius.

42. The improvement of claim 36 wherein said method further comprises mixing another polyanhydride with said first mentioned polyanhydride, said second polyanhydride being chosen from the group consisting of pyromellitic dianhydride, benzophenone dianhydride, and a norbornene polycarboxylic acid anhydride.

43. In the method of foaming an imide polymer by mixing an isocyanate and a polyanhydride oligomer in the presence of a catalyst, the improvement wherein said polyanhydride oligomer is chosen from the group consisting of diamic acid polyanhydrides and diimide polyanhydrides, and wherein said polymer is foamed to a density of from one to thirteen pounds per cubic foot.

44. The improvement of claim 43 wherein said polyanhydride oligomer is mixed with a water-insoluble ammonium polyphosphate.

45. The improvement of claim 43 wherein said polyanhydride oligomer has the structure:

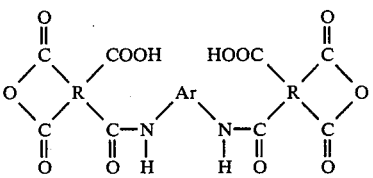

where R is a substituted or unsubstituted alicyclic, polyalicyclic, aromatic or polyaromatic group and Ar is a substituted or unsubstituted aromatic or polyaromatic group.

46. The improvement of claim 45 wherein Ar includes two aromatic rings, each nitrogen linkage shown in claim 36 being to a different one of said aromatic rings, each of said two aromatic rings being substituted, in a position ortho to the nitrogen linkage, by a halogen.

47. The improvement of claim 46 including a further step of heating said polymer to a temperature of at least about 200 degrees Celsius to remove said halogens and convert said polymer to a cardopolymer.

48. The improvent of claim 43 wherein said imide foam is filled wit an inorganic filler.

49. In the method of forming an imide polymer by mixing an isocyanate and a polyanhydride oligomer in the presence of a catalyst, the improvement wherein said polyanhydride oligomer comprises a norbornene anhydride.

50. The method of claim 49 wherein the norbornene anhydride is a polymerized cis-5-norbornene-2,3-dicarboxylic acid anhydride.

51. A high temperature resistant polymer consisting of repetitive units, each of said units comprising an amic acid group and a halogen atom, said amic acid group consisting of a carboxyl group and a singly substituted amide linkage attached to adjacent carbon atoms, said amic acid group closing on application of heat to provide an imide linkage, said halogen atom being removable by the application of heat to cross-link at least some of said units to form a cardopolymer.

52. A high temperature resistant polymer consisting of repetitive units, each of said units comprising a plurality of aromatic rings, over ninety percent of the molecular weight of the unit being part of a ring structure or being attached directly to a ring structure, or being part of an amic acid group, and a halogen atom attached to at least one of said aromatic rings of each unit, said halogen atom being removable by the application of heat to cross-link at least some of said units to form a cardopolymer.

53. The polymer of claim 52 wherein said units are linked to each other by imide linkages.

54. A method of producing a polymer comprising a first step of forming a substantially pure trimer by reacting an aromatic or alicyclic dianhydride reactant with an aromatic primary diamine reactant, and controlling the reaction conditions to provide a substantially pure trimer comprising two identical reactive terminal parts derived from one of said reactants and a central part derived from the other of said reactants, thereafter a second step of recovering said trimer as a solid, and thereafter a third step of reacting said solid trimer with a difunctional reactant to form a polymer.

55. The method of claim 54 wherein at least one of said dianhydride and diamine reactants is carried by a solvent in which it is poorly soluble.

56. The method of claim 54 wherein said oligomer includes amic acid groups at other than terminal positions.

57. The method of claim 56 wherein said amic acid groups each include a nitrogen atom attached to an aromatic ring, said aromatic ring being substituted in a position ortho to the nitrogen linkage.

58. The method of claim 57 wherein at least 90% of the molecular weight of said oligomer consists of atoms forming ring structures, or atoms attached directly to ring structures, or atoms forming said amic acid groups.

59. The method of claim 58 wherein said oligomer has a molecular weight of from 600 to 1000 and a softening temperature of from 20° C. to 80° C.

* * * * *

UNITED STATES PATENT AND TRADEMARK OFFICE
CERTIFICATE OF CORRECTION

PATENT NO.  : 4,687,785
DATED       : August 18, 1987
INVENTOR(S) : Parker, et al It is certified that error appears in the above—identified patent and that said Letters Patent is hereby corrected as shown below:

Col. 3   Line 55   "slighly"   should be   "slightly"

Claim 48  Col. 15  Line 36   "wit"   should be   "with"

Signed and Sealed this

Nineteenth Day of April, 1988

Attest:

DONALD J. QUIGG

Attesting Officer

Commissioner of Patents and Trademarks